(12) United States Patent
Cheng et al.

(10) Patent No.: US 7,301,339 B1
(45) Date of Patent: Nov. 27, 2007

(54) ESTIMATING THE CONCENTRATION OF A SUBSTANCE IN A SAMPLE USING NMR

(75) Inventors: Yuesheng Cheng, Edmonton (CA); Abdel M. Kharrat, Edmonton (CA); Krishnamurthy Ganesan, Sugar Land, TX (US); Robert Freedman, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/616,220

(22) Filed: Dec. 26, 2006

(51) Int. Cl.
*G01V 3/00* (2006.01)
(52) U.S. Cl. .................................. 324/303; 324/308
(58) Field of Classification Search ............... 324/303, 324/308, 306, 300
See application file for complete search history.

(56) References Cited

U.S. PATENT DOCUMENTS

| | | | |
|---|---|---|---|
| 5,739,038 A * | 4/1998 | Burrows | 436/113 |
| 6,140,817 A | 10/2000 | Flaum et al. | |
| 6,274,865 B1 | 8/2001 | Schroer et al. | |
| 6,346,813 B1 | 2/2002 | Kleinberg | |
| 7,117,100 B2 * | 10/2006 | Venkataraman et al. | 702/27 |
| 2004/0254732 A1 | 12/2004 | Storm, Jr. et al. | |
| 2005/0182566 A1 | 8/2005 | DiFoggio | |
| 2005/0216196 A1 | 9/2005 | Akkurt et al. | |
| 2005/0221495 A1 * | 10/2005 | Bell et al. | 436/60 |
| 2006/0076132 A1 | 4/2006 | Nold, III et al. | |

OTHER PUBLICATIONS

Bouton, J. et al., Assessment of Sample Contamination by Downhole NMR Fluid Analysis, SPE 71714, Society of Petroleum Engineers, Sep. 30-Oct. 3, 2001, pp. 1-10.

* cited by examiner

*Primary Examiner*—Louis M. Arana
(74) *Attorney, Agent, or Firm*—Bryan L. White; Kevin P. McEnaney; Dale V. Gaudier

(57) ABSTRACT

A method for estimating a concentration of a substance in a test sample of formation fluid, comprising measuring an NMR parameter of a first sample of formation fluid to obtain a first measurement, adding a known quantity of the substance to the first sample to produce a modified sample, measuring the NMR parameter of the modified sample to obtain a second measurement; and determining a relation between the concentration of the substance and a function of the NMR parameter using the first and second measurements and the NMR parameter of the substance.

25 Claims, 9 Drawing Sheets

ESTIMATING THE CONCENTRATION OF A SUBSTANCE IN A SAMPLE USING NMR

BACKGROUND

1. Field

The invention relates generally to fluid characterization using nuclear magnetic resonance (NMR) instruments.

2. Background Art

The oil and gas industry has developed various tools capable of determining and predicting earth formation properties. Among different types of tools, nuclear magnetic resonance (NMR) instruments have proven to be invaluable. NMR instruments can be used to determine formation properties, such as the fractional volume of pore space and the fractional volume of mobile fluid filling the pore space. A general background of NMR well logging is described in U.S. Pat. No. 6,140,817.

NMR is a phenomenon resulting from interactions between nuclei and magnetic fields. When nuclei, which may have magnetic nuclear moments, i.e., non-zero spin angular momentum, are placed in a magnetic field $B_0$, assumed in the z-direction, two energy levels are formed corresponding to the nuclear magnetic moment oriented along and against $B_0$, respectively. Transitions between the two energy levels result in an electromagnetic signal characterized by the Larmor frequency, $\omega_0 = \gamma B_0$, where $\gamma$ is the gyromagnetic ratio of the nucleus and is a characteristic property of a nuclear species. The Larmor frequency is also the precession frequency of the nucleus in the magnetic field.

For a group of nuclei at equilibrium in a static magnetic field $B_0$, the net magnetization vector (due to nuclear spin) is along the direction of $B_0$. The nuclei can be excited to a higher energy level, e.g., by an RF pulse. The excited nuclei tend to relax to their equilibrium state in the direction of $B_0$. The time constant associated with this relaxation process is referred to as the spin-lattice relaxation time, or longitudinal relaxation time ($T_1$), which is a characteristic time for the longitudinal magnetization $M_z$.

For nuclei having a magnetization component in the x-y plane, the nuclei will have a precession motion in the x-y plane. The net magnetization in the x-y plane de-phases on a time scale $T_2$, called the spin-spin relaxation time, or transverse relaxation time.

Borehole fluid sampling and testing tools such as Schlumberger's Modular Dynamics Testing (MDT) Tool can provide important information on the type and properties of reservoir fluids in addition to providing measurements of reservoir pressure. These tools may perform measurements of the fluid properties downhole, using sensor modules on board the tools. Alternatively, these tools can withdraw fluid samples from the reservoir that can be collected in vessels and brought to the surface for analysis. The collected samples are routinely sent to fluid properties laboratories for analysis of physical properties that include, among other things, oil viscosity, gas-oil ratio, mass density or API gravity, molecular composition, $H_2S$, asphaltenes; resins, and various other impurity concentrations. However, if the samples are contaminated by mud filtrate, the laboratory data may not be useful or relevant to the reservoir fluid properties.

For example, the collected fluid samples could be emulsions of filtrate water and crude oil or, in wells drilled with oil-base muds, mixtures of reservoir crude oil and oil-base mud filtrate (OBMF). In either case the contamination may render the measured laboratory data irrelevant to the actual properties of the in situ reservoir fluids. In order for fluid sampling tool or laboratory measurements of reservoir fluid samples to be relevant, the samples must have low levels of contamination. In those cases where the samples brought to the surface have low or negligible contamination, laboratory results can still be tainted (e.g., by precipitation of solids caused by temperature changes).

It is well known that the reservoir fluid samples taken should avoid contamination from drilling mud filtrate in order to yield pressure-volume-temperature (PVT) properties that are truly representative of the native fluids. Furthermore, knowledge of accurate contamination levels is critical because too much contamination can lessen or negate the value of PVT laboratory measurements made on fluid samples, as well as downhole measurements made on such samples. Prior art methods disclose various methods for determining contamination levels, including measuring various physical properties of the fluid mixture. For example, U.S. Patent Application Publication US 2004/0254732 A1 by Storm et al. and U.S. Patent Application Publication US 2005/0182566 A1 by DiFoggio disclose methods and apparatus for determining the extent of contamination by measuring density. U.S. Pat. No. 6,274,865 B1 issued to Schroer et al. discloses methods and apparatus for determining the extent of contamination by measuring optical density.

Prior art methods use either mixing law equations or other empirical equations, which require knowledge of endpoint fluid properties (e.g., densities of the oil-base mud filtrate and the native oil) for quantitative estimation of contamination. However, in practice, there is usually at most one reliably known endpoint, i.e., that corresponding to 100% contamination. The endpoint corresponding to the native hydrocarbon (0% contamination) is generally not known. Without both endpoints, the estimation of contamination using prior art methods may only be qualitatively accurate.

There are other prior art methods that attempt to predict contamination from NMR measurements. The "sharpness" of an NMR relaxation time distribution was introduced as an indicator of OBMF contamination by Bouton, J. et al. (SPE Paper 71714 presented at the ATCE in New Orleans, La., 2001). This method is not reliable because it assumes that only OBMFs have a narrow relaxation time distribution. On the contrary, it is well known that low-viscosity crude oils, water, and gas also have narrow relaxation time distributions. U.S. Patent Application Publication 2005/0216196 A1 by Akkurt et al. discloses a method based on a family of different viscosity mixing laws and temporal contamination models. However, there are at least two drawbacks to the Akkurt et al. teachings: (1) the viscosity mixing laws disclosed by Akkurt et al. have not been shown to be valid for crude oils mixed with OBMF and, moreover, the different mixing laws predict different contaminations for the same mixture; (2) mixing laws require knowledge of the native oil properties (i.e., 0% contamination), which are generally not available in practical applications.

As described above, there is a need for a more direct and robust method for determining the level of OBMF contamination while the fluid is still within reservoirs and under the reservoir conditions, as well as in a laboratory.

SUMMARY OF INVENTION

A method for estimating a concentration of a substance in a test sample of formation fluid, comprising measuring an NMR parameter of a first sample of formation fluid to obtain a first measurement, adding a known quantity of the substance to the first sample to produce a modified sample, measuring the NMR parameter of the modified sample to obtain a second measurement, and determining a relation between the concentration of the substance and a function of the NMR parameter using the first and second measurements and the NMR parameter of the substance.

In another aspect, a system for estimating a concentration of a substance in a test sample of formation fluid, comprising a mixer configured to add a known quantity of the substance to a first sample of formation fluid to produce a modified sample; an NMR measurement device configured to measure an NMR parameter of the first sample and the modified sample to obtain a first measurement and a second measurement, and a processor configured to determine a relation between the concentration of the substance and a function of the NMR parameter using the first and second measurements and the NMR parameter of the substance.

In another aspect, a downhole tool for estimating a concentration of a substance in a test sample of formation fluid, comprising a tool body adapted to be placed in a borehole, a mixing module disposed in the tool body and configured to add a known quantity of the substance to a first sample of formation fluid to produce a modified sample, an NMR module disposed in the tool body and configured to measure an NMR parameter of the first sample and the modified sample, and a processor disposed in the tool body and configured to determine a relation between the concentration of the substance and the NMR parameter.

Other aspects and advantages of the invention will be apparent from the following description and the appended claims.

DETAILED DESCRIPTION

Figure 1:
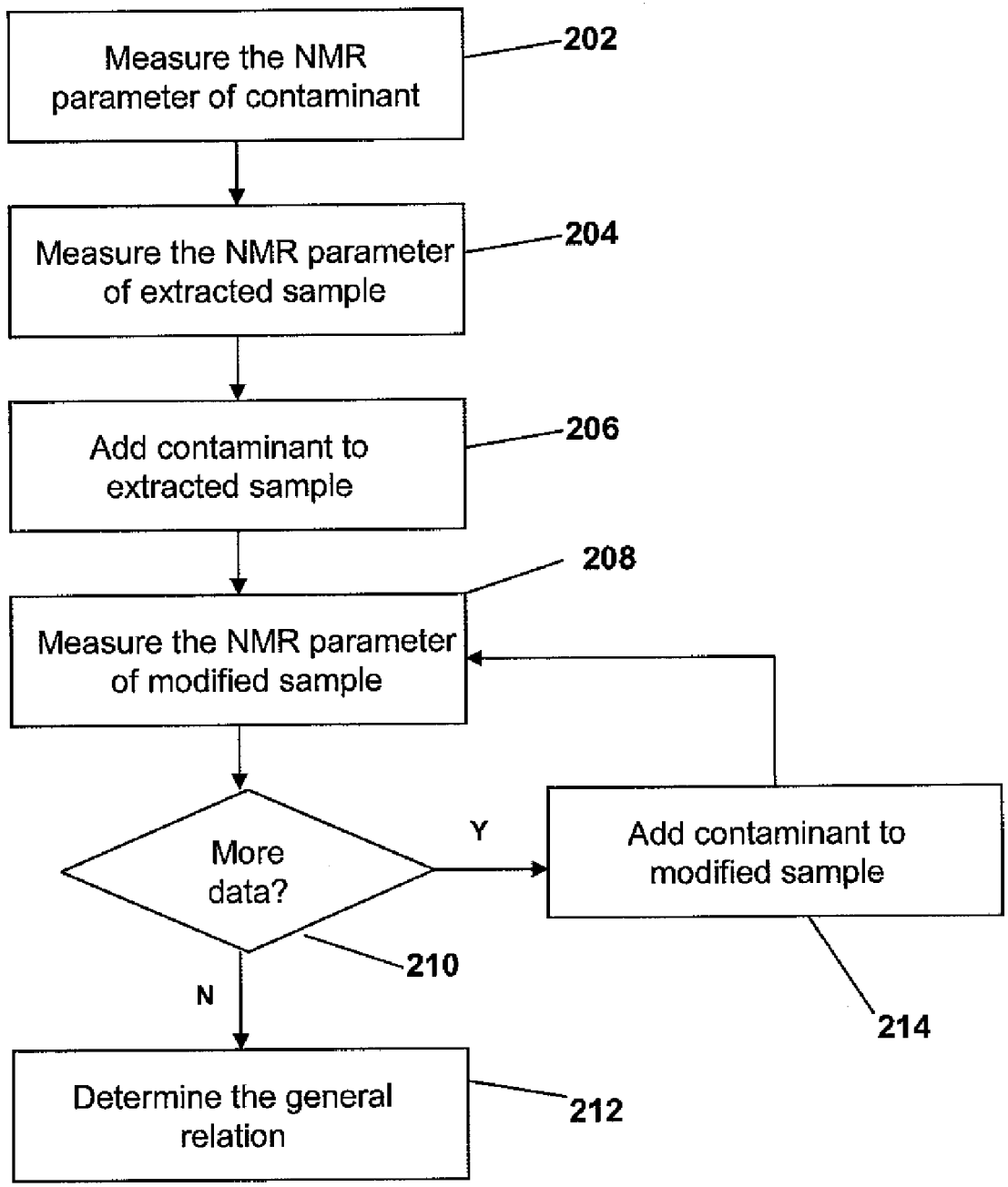
FIG. 1 shows a method for determining a general relation between the concentration of a substance and an NMR parameter in accordance with one or more embodiments of the present invention.

Specific embodiments of the invention will now be described in detail with reference to the accompanying figures. Like elements in the various figures may be denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention relate to a method and apparatus for estimating the concentration of a known contaminant in a formation fluid sample using NMR measurements. For fluid sampling tool measurements or laboratory measurements on formation fluid samples to be relevant, the samples should have low levels of contamination. Knowledge of accurate contamination levels is critical because too much contamination can lessen the value of pressure-volume-temperature (PVT) laboratory measurements made on fluid samples, as well as downhole measurements made on such samples. In one or more embodiments of the invention, NMR measurements are used to determine the oil-base mud filtrate (OBMF) contamination in a mixture of crude oil and OBMF. Furthermore, a method and apparatus of the present invention may be implemented in a laboratory or downhole.

FIG. 1 shows a method for obtaining data points and determining a general relation between the concentration of a known contaminant and an NMR parameter in accordance with one or more embodiments of the present invention. NMR parameter includes, but is not limited to, $T_1$, $T_2$, diffusion constant, hydrogen index, and viscosity. In accordance with this method, an NMR parameter of a pure sample of the known contaminant is measured (step 202). The measured NMR parameter of the known contaminant gives the data point relating to 100% contamination in the general relation, and thus gives one endpoint of the general relation. In practice, the endpoint relating to 100% contamination may be the only endpoint that can practically be found. Thus, further data points in the general relation may be obtained by measuring the NMR parameter of an extracted sample of the formation fluid and modified samples.

Accordingly, the NMR parameter of an extracted sample of the formation fluid is measured to obtain a second data point of the general relation (step 204). Next, the extracted sample is modified by adding a known quantity of the known contaminant to a known quantity of the extracted sample to produce a modified sample (step 206). The NMR parameter of the modified sample is measured to obtain a third data point of the general relation (step 208). A determination of whether more data points are desired may be made at this point (step 210). If no further data points are desired, the general relation may then be determined (step 212). Otherwise, a known quantity of the known contaminant may be added to the modified sample to produce a further modified sample (step 214). The method may then return to step 208 to measure the NMR parameter of the further modified sample.

Determining a general relation between the concentration of the known contaminant and the NMR parameter may require that the change in concentration of the known contaminant between obtained data points is known. The second and third data points (and further obtained data points) are related by a known change in quantity of the contaminant in the extracted sample and the modified sample, but the absolute change in concentration may not be known. Rather, the change in concentration between the extracted and modified samples may be approximated. The change in contamination may be expressed as $$c_1 - c = \frac{w_{CONT} + w_1}{w + w_1} - \frac{w_{CONT}}{w} = \frac{w_1}{w + w_1}(1 - c), \quad (1)$$

where $c$ and $c_1$ are the concentrations of the known contaminants in the extracted and modified samples, respectively, w is the total weight of the extracted sample, $w_{CONT}$ is the weight of the known contaminant in the extracted sample (unknown), and $w_1$ is the weight of the known contaminant added to the extracted sample. If it is assumed that the contamination c of the extracted sample is small (e.g., less than 10%) then the change in concentration may be expressed as $$c_1 - c \cong \frac{w_1}{w + w_1}. \quad (2)$$

The assumption that the contamination c of the extracted sample is small is not a limitation in practice because modern fluid sampling tools are designed to quickly achieve contamination levels below 10% after relatively short pumpout periods in most environments. Once the change in concentration between samples has been approximated, the general relation may be determined in several different ways depending on the nature of the general relation. The general relation may be linear or non-linear. If the general relation is linear, for example, a method for determining the linear relation is explained with reference to FIG. 2.

Figure 2:
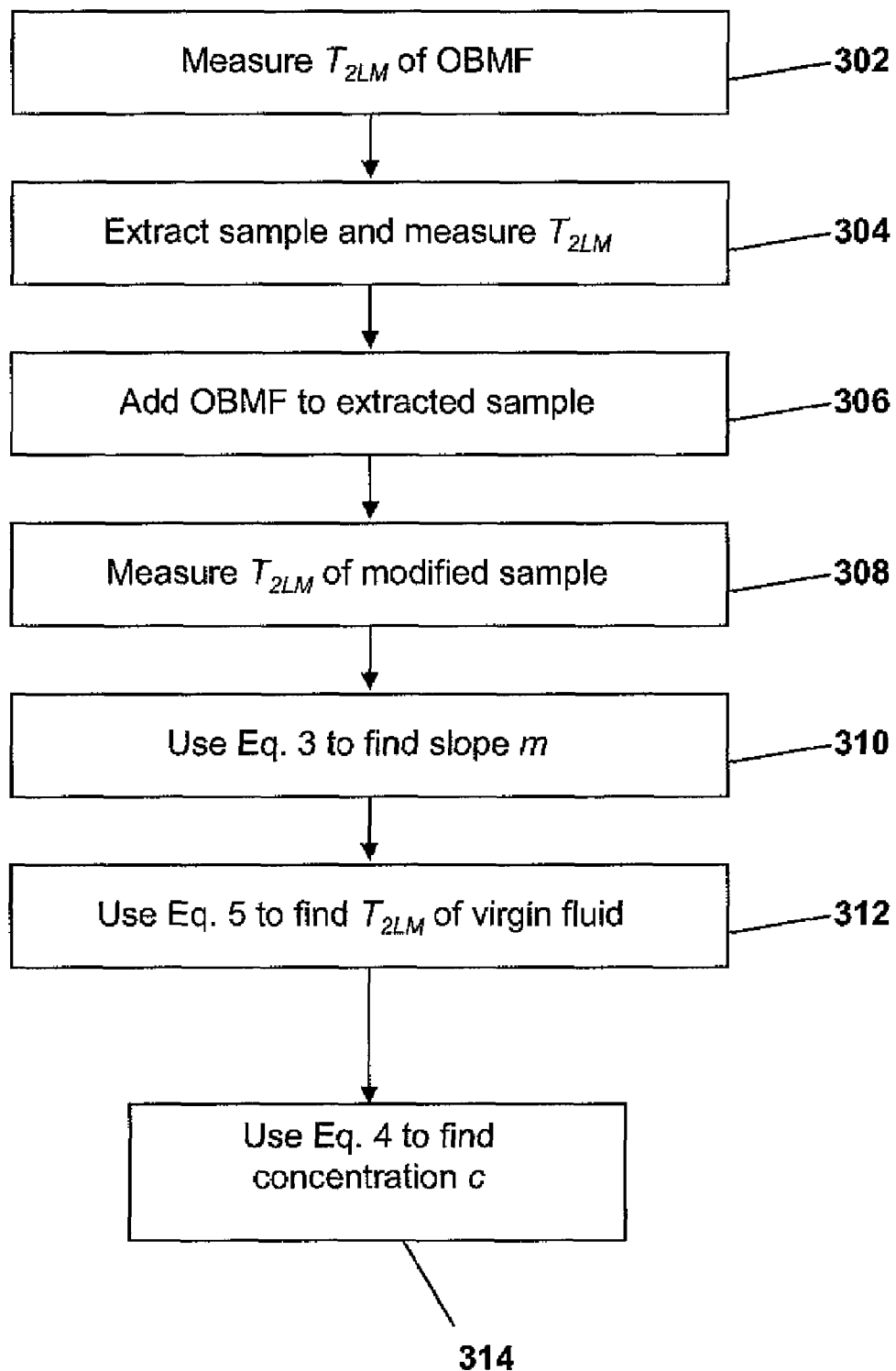
FIG. 2 shows a method for estimating the concentration of a substance in accordance with one or more embodiments of the present invention.

FIG. 2 shows the steps for estimating the concentration of a contaminant in a formation fluid in accordance with one or more embodiments of the present invention. In this example, the known contaminant is a known oil-base mud filtrate (OBMF) that may be used to drill a well containing a native hydrocarbon fluid as known in the art. However, the invention is not limited in application to only this contaminant. The sampled formation fluid is usually a mixture of OBMF and the native hydrocarbon fluid. The NMR parameter to be measured is, in this embodiment, the logarithmic mean of the spin-spin relaxation time ($T_{2LM}$). However, the logarithmic mean of the longitudinal relaxation time ($T_{1LM}$) could be measured instead of $T_{2LM}$. The concentration of OBMF in the sampled formation fluid is approximately linearly related to the logarithm of $T_{2LM}$ of the mixture, and thus the general relation is linear in concentration. A linear relation between the concentration of OBMF and the logarithm of $T_{2LM}$ may be determined by defining an endpoint and the slope of the linear relation.

In accordance with this method, the logarithmic mean of the $T_2$ distribution spectrum of a sample of the OBMF ($T_{2LM}^{OBM}$) is obtained by an NMR measurement device (step 302). The logarithm of $T_{2LM}^{OBM}$ defines one endpoint of the linear relation because the sample of OBMF corresponds to 100% contamination.

A first sample of the formation fluid is extracted (step 304). As previously disclosed, the first sample may be extracted by a downhole tool and then transported to the surface such that the remainder of the method may be practiced in a laboratory. Alternatively, the first sample may be extracted into a fluid sampling tool configured to practice the remainder of the method downhole. After acquiring the first sample, the logarithmic mean of the $T_2$ distribution spectrum of the first sample ($T_{2LM}^{1st}$) is obtained by the NMR measurement device, and another data point in the linear relation is defined as the logarithm of $T_{2LM}^{1st}$. The first sample has a concentration c of the OBMF contaminant.

A known quantity $w_1$ of the OBMF is added to a known quantity w of the first sample to produce a modified sample (step 306). The modified sample has a concentration $c_1$ of the OBMF, which is increased relative to the concentration c of the first sample. Further, the logarithmic mean of the $T_2$ distribution spectrum of the modified sample ($T_{2LM}^{mod}$) is obtained by the NMR measurement device, and another data point in the linear relation is defined as the logarithm of $T_{2LM}^{mod}$ (step 308). It is important that the quantities of the first sample and the added OBMF are known so that the change in concentration of the OBMF between the first sample and the modified sample may be approximated.

The slope of the linear relation may be determined from any two of the data points. For example, a plot of the linear relation may have a y-axis corresponding to the logarithm of the logarithmic mean of the $T_2$ distribution spectrum of any sample of the formation fluid ($\ln T_{2Lm}^{mix}$), and the plot of the linear relation may have an x-axis corresponding to the concentration of contaminant c. Thus, the slope of the linear relation is the quotient of the change in $\ln T_{2LM}^{mix}$ and the change in c. The slope of the linear relation may be expressed as $$m = (\ln T_{2LM}^{mod} - \ln T_{2LM}^{1st}) \frac{(w + w_1)}{w_1}, \quad (3)$$

where m is the slope of the linear relation (step 310). The second term in the product of Eq. 3 is from Eq. 2, which assumes that the concentration c of the OBMF in the first sample is small. Again, this is not a limitation in practice because modern fluid sampling tools are designed to achieve contamination levels below 10%. Accordingly, samples of the formation fluid may be extracted to have contamination levels (i.e., concentration of OBMF) below 10%.

One endpoint of the linear relation (100% contamination) and the slope of the linear relation have been defined, allowing for determination of the linear relation. The linear relation may be expressed as $$\ln(T_{2LM}^{mix}) = \ln(T_{2LM}^V) + c^*m, \quad (4)$$

where $\ln T_{2LM}^V$ is the logarithm of the logarithmic mean of the $T_2$ distribution spectrum of the native, or virgin, hydrocarbon fluid, which defines the second endpoint, c is the concentration of the OBMF contaminant expressed as a percentage, and m is the slope of the linear relation. The derivation of Eq. 4 is disclosed under the section titled, "Derivation of the Linear Relation."

By obtaining the second endpoint relating to 0% contamination, the linear relation may be completely determined. The second endpoint may be calculated according to Eq. 5 below (step 312).

$$\ln T_{2LM}^V = \ln T_{2LM}^{OBM} - m^*100 \quad (5)$$

Once the linear relation has been determined, the concentration c of the OBMF contaminant in the first sample may be determined by solving for c in Eq. 4 (step 314). Similarly, the linear relation may be applied to any sample of the formation fluid. For example, the logarithm of the logarithmic mean of the $T_2$ distribution spectrum of another sample may be measured and substituted for $\ln T_{2LM}^{mix}$ in Eq. 4. Then, the unknown concentration c of the OBMF contaminant may be solved for using Eq. 4.

The method shown in FIG. 2 includes obtaining data points related to the extracted sample and the modified sample. In other embodiments, it may be desired to obtain more data points such that the linear relation may be more accurate. For example, steps 306 and 308 may be repeated such that a plurality of modified samples are produced. Furthermore, the logarithm of the logarithmic mean of the $T_2$ distribution spectrum may be obtained for each modified sample, thus providing a plurality of data points relating to the modified samples. Because there may be more than two data points from which to determine the slope of the linear relation, another technique may be used to determine the slope from the data points. Those skilled in the art will appreciate that many mathematical techniques exist that may facilitate the determination of the linear relation from the data points of the extracted sample and the modified samples. For example, the linear least squares technique may be used to fit a line to the data points of the extracted sample and the modified samples. The slope of this line may then be used as the slope of the linear relation. The general relation is not, however, limited to a linear relation. The above-described method can be modified to cover the more general relation. Alternatively, the existing mathematical techniques, such as non-linear least squares, can be used to determine the parameters of the general relation.

Figure 3:
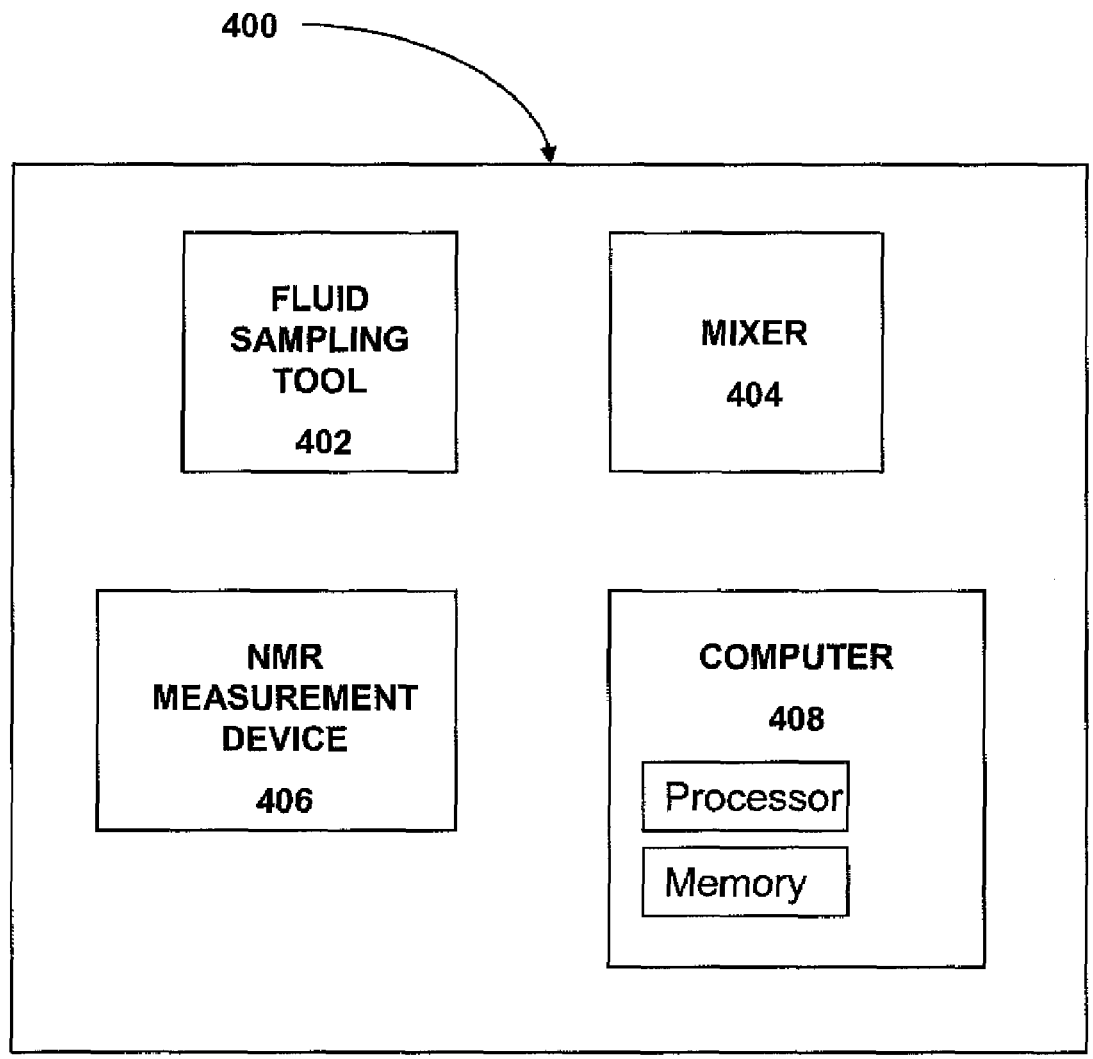
FIG. 3 shows a system for estimating the concentration of a substance in accordance with one or more embodiments of the present invention.

FIG. 3 shows a system 400 for estimating the concentration of a known contaminant in a sample of a formation fluid in accordance with one or more embodiments of the present invention. It is often desired that the concentration of the known contaminant in the formation fluid be estimated such that properties of a native fluid may be determined. For example, the known contaminant may be a known oil-base mud filtrate (OBMF) that has invaded an oil bearing rock formation in a well drilled with an oilbase drilling mud. The formation fluid may be a mixture of the OBMF and the native hydrocarbon fluid. Furthermore, the system 400 may be used in accordance with the previously disclosed method.

The system 400 according to this embodiment includes a fluid sampling tool 402 configured to extract a sample of the formation fluid and carry it to the surface, whereby the extracted sample may then be transported to a laboratory or another setting where the concentration of the known contaminant can be estimated. The system 400 further includes a mixer 404 configured to mix a specified quantity of the known contaminant with the extracted sample to produce a modified sample having a higher concentration of the known contaminant than the extracted sample. The mixer 404 may also mix a known quantity of the known contaminant with the modified sample to produce further modified samples. Furthermore, the system 400 includes an NMR measurement device 406 configured to measure an NMR parameter in a sample of a fluid. For example, the NMR measurement device 406 may be used to measure the NMR parameter of the known contaminant, the extracted sample, and any modified samples. NMR measurement devices are well known in the art, and the NMR measurement device 406 may be similar to any practical NMR measurement device thus known. Additionally, acquisition of NMR measurements according to embodiments of the present invention may be accomplished with various methods of NMR measurements known in the art.

Also, the system 400 includes a computer 408 having a processor and a memory. The computer 408 is configured to determine a general relation between the concentration of the known contaminant and the NMR parameter according to the previously disclosed method. For example, the processor of the computer 408 may be programmed with instructions enabling the computer 408 to perform the previously disclosed method. The measured NMR parameters may be stored in the memory of the computer 408, and the general relation may also be stored in the memory of the computer 408 after it is determined.

Once the determined relation is stored in the memory of the computer 408, the determined relation may be used to estimate the concentration of the known contaminant in any sample of the formation fluid, including the original sample from which the relation was determined. For example, further samples may be extracted by the fluid sampling tool 402, and then the NMR measurement device 406 may be used to measure the NMR parameters of the extracted samples. The computer 408 may then use the measured NMR parameters of the extracted samples with the determined relation to estimate the concentration of the known contaminant in the extracted samples in accordance with the previously disclosed method.

The fluid sampling tool 402 of the system 400 may be any tool configured to extract a sample of formation fluid. Ideally, the concentration of the known contaminant will be below 10% such that the assumption of Eq. 2 holds true. One such tool is disclosed in U.S. Patent Application Publication No. 2006/0076132 assigned to the assignee of the present invention.

Figure 4:
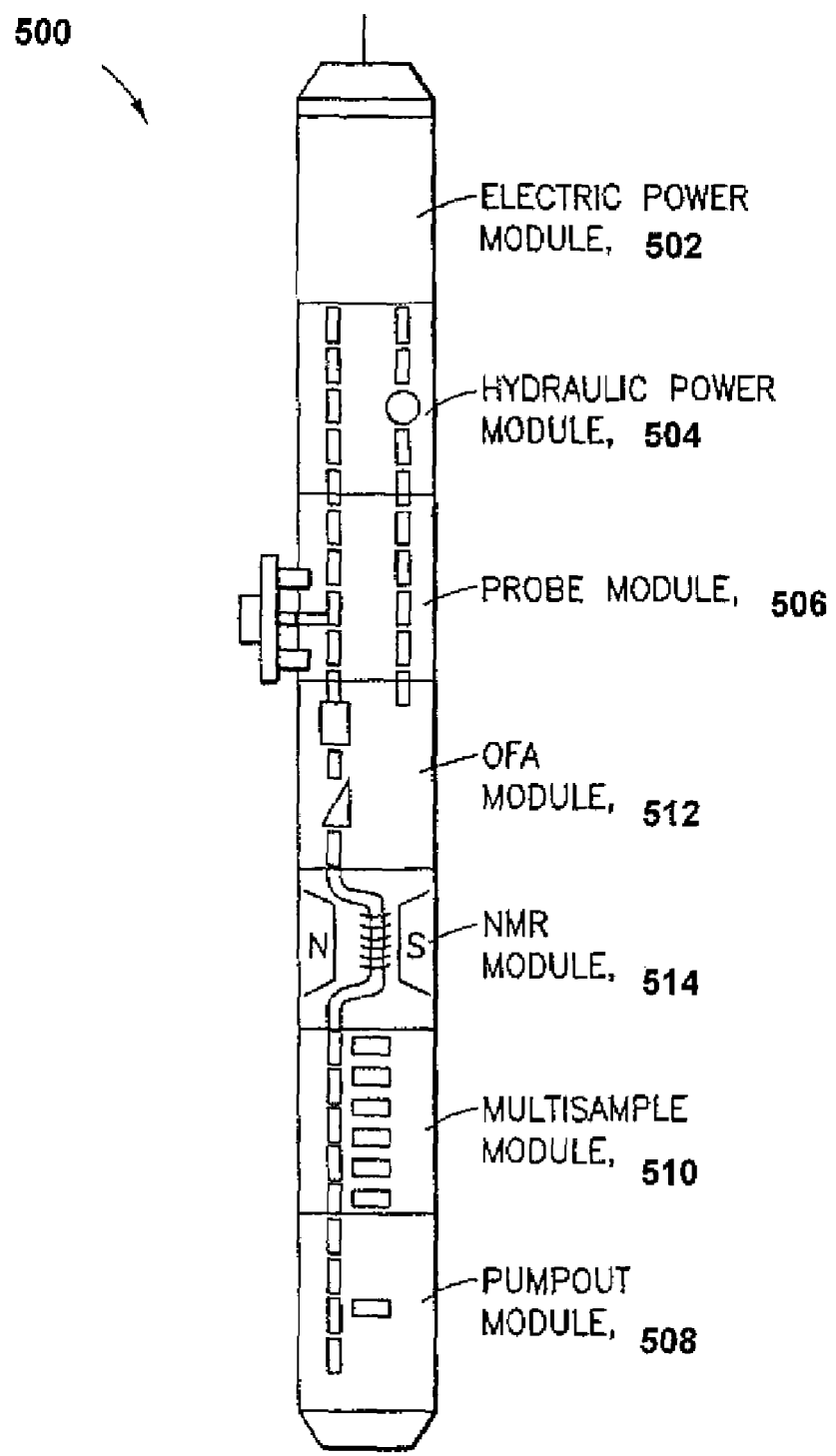
FIG. 4 shows a prior art fluid sampling tool.

FIG. 4 shows a prior art fluid sampling tool 500 taken from U.S. Pat. No. 6,346,813 issued to Kleinberg ("Kleinberg '813") and assigned to the assignee of the present invention. Kleinberg '813 is hereby incorporated by reference in its entirety. An embodiment of the fluid sampling tool 500 may be used as the fluid sampling tool 402. The fluid sampling tool 500, containing some elements similar to Schlumberger's Modular Dynamics Testing Tool (MDT), comprises several parts that enable extraction of fluids from permeable earth formations. As shown, the fluid sampling tool 500 in accordance with this embodiment includes the following modules: an electronic module 502, which may include a processor and a memory; a hydraulic power module 504; a probe module 506, which may be deployed to make a hydraulic seal with the formation; a pumpout module 508; and a multisample module 510. When used with the system 400, the fluid sampling tool 500 may extract one or more samples of the formation fluid and transport the extracted samples to the surface in the multisample module 510. Additionally, the fluid sampling tool 500 may include an optical fluid analyzer (OFA) 512 and an NMR module 514. The OFA 512 and the NMR module 514 may facilitate extraction of samples having a low concentration of the contaminant, as disclosed in Kleinberg '813.

The fluid sampling and testing tool 500 may extract a sample of the formation fluid, the NMR module 514 may measure the NMR parameter of the extracted sample, and then the processor of the electronic module 502 may use the measured NMR parameter and the stored relation to estimate the concentration of the known contaminant in the extracted sample. Thus, samples of the formation fluid may be tested downhole rather than extracting the samples to the surface for testing.

Various NMR modules are known in the art, and thus the NMR module 406 may be similar to those known in the art. For example, an NMR module 406 in accordance with an embodiment of the invention may include (1) a magnet (e.g., a permanent magnet) that is designed to produce a static magnetic field in the flowline (flow pipe) of the fluid sampling and testing tool 402, and (2) an RF antenna (which may function as a transmitter and a receiver) designed to radiate an oscillating magnetic field having its magnetic dipole substantially perpendicular (orthogonal) to that of the static magnetic field. The frequency of the oscillating magnetic field may be selected to be equal to the Larmor frequency of the NMR sensitive nuclei (e.g., $^1H$ or $^{13}C$) under investigation. Because of signal-to-noise considerations, it is preferred to measure $^1H$ nuclei in rapidly flowing fluids. For stationary measurements (i.e., when fluid is not flowing), signals from other nuclei, including $^{13}C$ may be measured. One of ordinary skill in the art would appreciate that the same RF antenna may function as a transmitter to transmit the oscillating magnetic field and as a receiver to receive the signals, as disclosed in Kleinberg '813. Alternatively, separate transmitter and receiver antennas may be used. The magnet may have a pre-polarization region for polarizing the fluid before it enters the transmitter/receiver antenna region. The pre-polarization may be necessary for obtaining measurable signals from rapidly moving nuclei.

Figure 5:
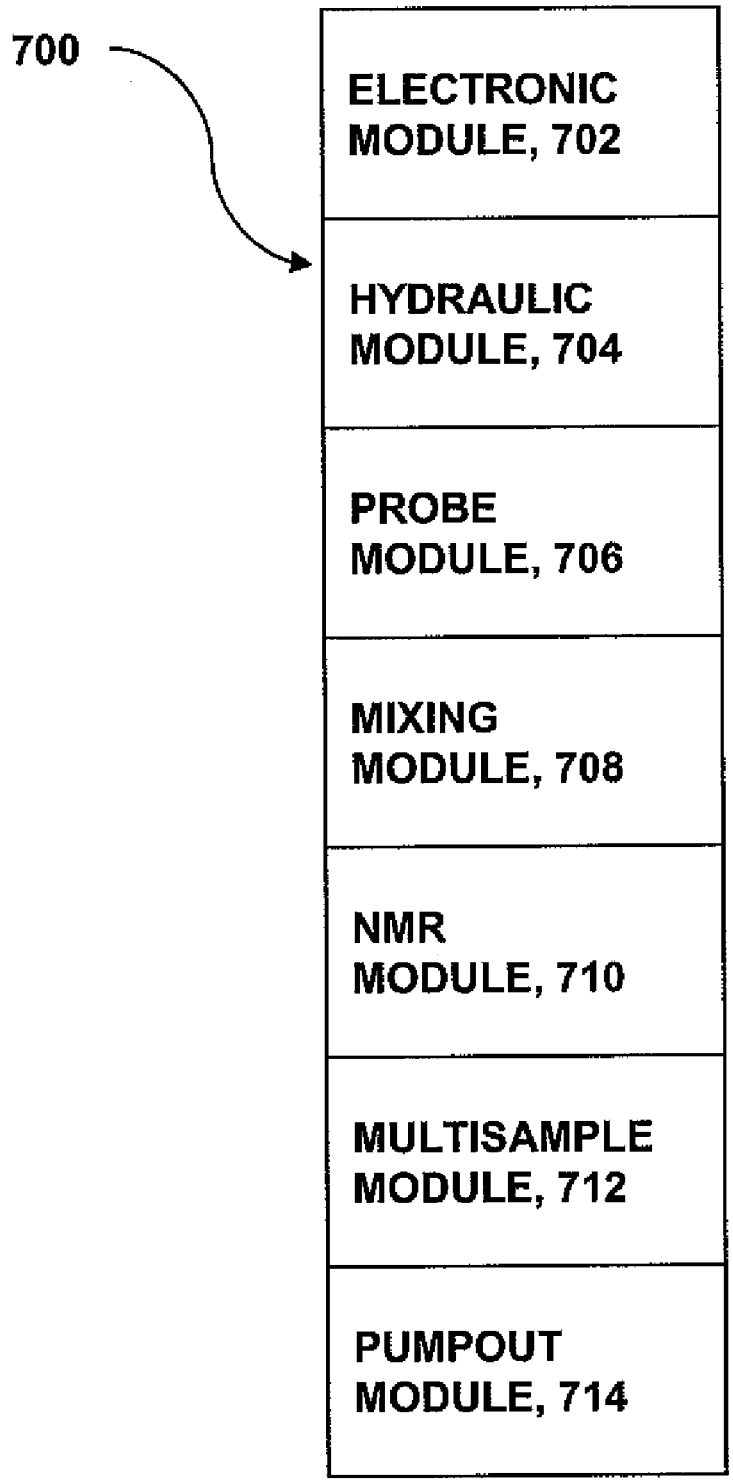
FIG. 5 shows a fluid testing tool in accordance with one or more embodiments of the present invention.

FIG. 5 shows a fluid testing tool 700 for estimating the concentration of a known contaminant in a sample of a formation fluid in accordance with one or more embodiments of the present invention. As shown, the fluid testing tool 700 includes a tool body adapted to be placed in a borehole that includes the following modules: an electronic module 702, which includes a processor and a memory; a hydraulic power module 704; a probe module 706, which may be deployed to make a hydraulic seal with the formation; a mixing module 708; an NMR module 710; a multi-sample module 712; and a pumpout module 714. The fluid testing tool 700 may be substantially similar to the previously disclosed downhole tools. However, the fluid testing tool in this embodiment includes the mixing module 708 such that the invention may be performed in its entirety downhole.

The fluid testing tool 700 may be used to extract a sample of the formation fluid through the probe module 706 into the flowline of the fluid testing tool 700. From there, a portion of the extracted sample passes through the mixing module 708 unmodified into the NMR module 710. The NMR module 710 then measures the NMR parameter of the extracted sample. A second portion of the extracted sample, of a known quantity, remains in the mixing module 708 where a known quantity of the known contaminant is added to the second portion of the extracted sample to produce a modified sample. Further modified samples may similarly be produced. The modified sample then passes into the NMR module 710 where the NMR parameter of the modified sample is measured. The NMR parameter of the known contaminant may be measured prior to operation of the fluid testing tool 700 and stored in the memory of the electronic module 702, or it may be measured by the NMR module 710 during operation of the fluid testing tool 700.

The electronic module 702 may be configured to determine a general relation between the concentration of the known contaminant in the extracted sample and the NMR parameter according to the previously disclosed method. For example, the processor of the electronic module 702 may be programmed with instructions enabling the electronic module 702 to perform the previously disclosed method. The measured NMR parameters may be stored in the memory of the electronic module 702, and the general relation may also be stored in the memory of the electronic module 702 after it is determined.

Once the determined relation is stored in the memory of the electronic module 702, the determined relation may be used to estimate the concentration of the known contaminant in any sample of the formation fluid, including the original sample from which the relation was determined. For example, further samples may be extracted by the fluid testing tool 700, and then the NMR module 710 may be used to measure the NMR parameters of the extracted samples. The electronic module 702 may then use the measured NMR parameters of the extracted samples with the determined relation to estimate the concentration of the known contaminant in the extracted samples in accordance with the previously disclosed method.

Figure 6:
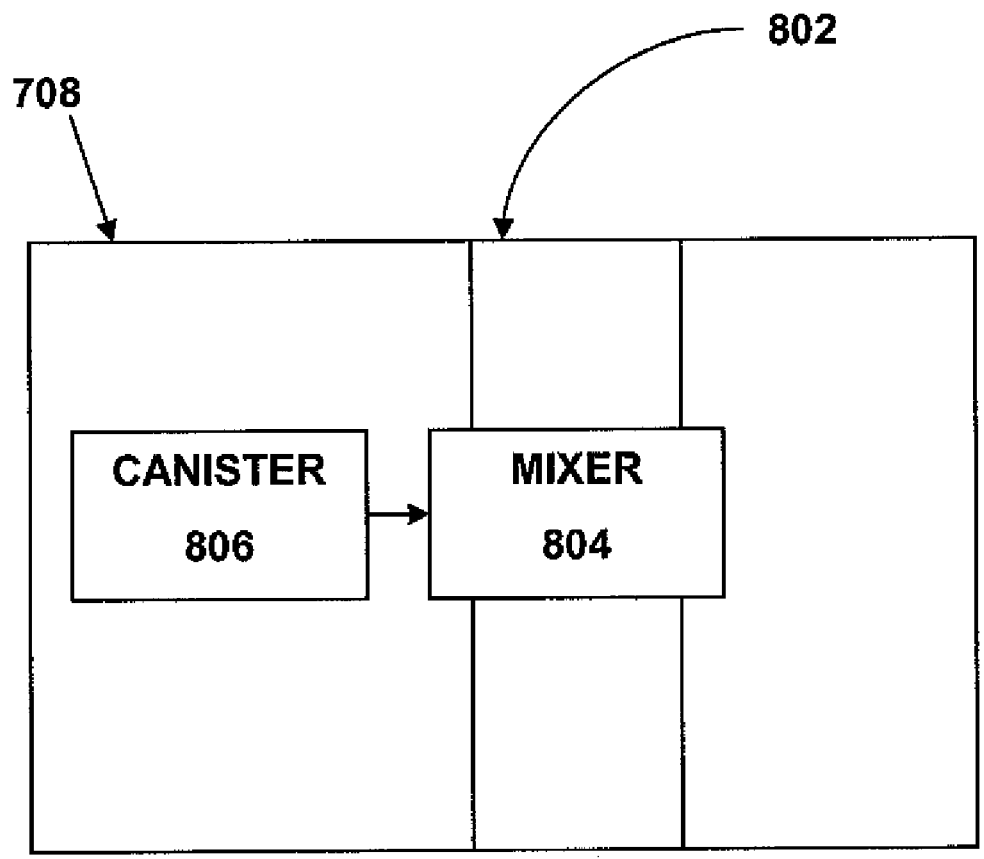
FIG. 6 shows a mixing module in accordance with one or more embodiments of the present invention.

FIG. 6 shows a mixing module 708 in accordance with one or more embodiments of the present invention. The mixing module 708 is configured to add a known quantity of a known contaminant to a known quantity of an extracted sample of a formation fluid. Additionally, the mixing module 708 may allow a portion of the extracted sample to pass unmodified through a flowline 802 of the mixing module 708. The mixing module 708 contains a mixer 804, which may draw (1) a specified quantity of the known contaminant from a canister 806 containing the known contaminant, and (2) a specified quantity of the extracted sample from the flowline 802. The mixer 804 then mixes the drawn contaminant with the drawn extracted sample to produce a modified sample. The modified sample then continues passage through the flowline 802. Operation of the mixing module 708 may be controlled by the electronic module 702.

Because the determination of the general relation and the estimation of the concentration of the known contaminant in an extracted sample are both performed downhole, downhole measurement conditions such as pressure and temperature should be close to that of the virgin (undisturbed) reservoir. Thus, downhole estimation of the concentration of the contaminant in a sample of the formation fluid may be more accurate.

Derivation of the Linear Relation

The method disclosed herein employs a general relation between the concentration of a contaminant and the logarithm of the logarithmic mean relaxation time of a mixture of a hydrocarbon fluid and a contaminant, which may be approximately linear. The linear approximation especially holds true when the concentration of the contaminant is small (e.g., less than 10%). However, test data has shown that the relation is still approximately linear for greater concentrations of a contaminant. Furthermore, the relaxation time of a hydrocarbon mixture obtained by NMR measurements may be the longitudinal relaxation time $T_1$ or the transverse relaxation time $T_2$. A derivation of the linear relation is disclosed below using $T_2$, but the same derivation similarly applies to $T_1$, which need only be substituted in the following equations for $T_2$.

The logarithmic mean of $T_2$ of an NMR $T_2$ distribution spectrum may be expressed as $$T_{2LM} = \left(\prod_{i=1}^{n} T_{2i}^{n_i}\right)^{\frac{1}{\sum_i n_i}}, \qquad (6)$$

and thus the logarithm of the logarithmic mean may be expressed as $$\ln(T_{2LM}) = \frac{\sum_i n_i \ln(T_{2i})}{\sum_i n_i}, \qquad (7)$$

where $n_i$ is the number of moles of protons corresponding to the ith component of $T_2$ in the $T_2$ distribution spectrum. Using a mole fraction expression, Eq. 7 becomes $$\ln(T_{2LM}) = \sum_i f_i \ln(T_{2i}), \qquad (8)$$

where $f_i$ is the mole fraction $$\frac{n_i}{\sum_i n_i}. \quad (9)$$

For a virgin oil (i.e., an oil having 0% OBMF contamination) the logarithm of the logarithmic mean of $T_2$ may be expressed as $$\ln(T_{2LM}^V) = \Sigma f_i^V \ln(T_{2i}^V), \quad (10)$$

and likewise, for a pure OBMF the logarithm of the logarithmic mean of $T_2$ may be expressed as $$\ln(T_{2LM}^{OBM}) = \Sigma f_i^{OBM} \ln(T_{2i}^{OBM}). \quad (11)$$

A mixture of OBMF and virgin oil may substantially follow the scaling law for alkanes, because it is generally true that most OBMFs and virgin oils contain a significant concentration of alkanes. When the OBMF is mixed with the virgin oil, the mole fraction of the OBMF is equal to the weight fraction, c, of the OBMF in the total alkane mixture, and the mole fraction of the virgin oil is equal to the weight fraction, 1−c, of the virgin oil in the total alkane mixture. Thus, the logarithm of the logarithmic mean of $T_2$ of the mixture may be expressed as $$\ln(T_{2LM}^{mix}) = \sum_i (1-c) f_i^V \ln(T_{2i}^{V,c}) + \sum_j c f_j^{OBM} \ln(T_{2j}^{OBM,c}) = \quad (12)$$
$$\sum_i f_i^V \ln(T_{2i}^{V,c}) + c \left( \sum_j f_j^{OBM} \ln(T_{2j}^{OBM,c}) - \sum_i f_i^V \ln(T_{2i}^{V,c}) \right).$$

Two of the terms in Eq. 12, $T_{2j}^{OBM,c}$ and $T_{2i}^{V,c}$, depend on properties of the mixture. However, it is desired that these terms be replaced by terms that depend on properties of the OBMF and the virgin oil, rather than the mixture. According to U.S. Patent Application Publication No. 2004/0253743 issued to Freed and assigned to the assignee of the present invention, relaxation time and molecule chain length are related by the equation $$T_{2i}(T,P) = B(T,P) N_i^{-k} \overline{N}^{-\gamma(T,P)}, \quad (13)$$

where $B(T,P)$ and $\gamma(T,P)$ are constant at a temperature T and a pressure P, k is the universal constant, $N_i$ is the chain length of the ith component in the $T_2$ spectrum, and $\overline{N}$ is the mean chain length of the mixture. Eq. 13 and the following derivations apply to dead oils, or oils that have a gas/oil ratio of zero. Those skilled in the art will appreciate that the following derivations may also be applied to live oils by modifying Eq. 13 to account for non-zero gas/oil ratios.

Considering only the second factor in the second term in Eq. 12, which is multiplied by c, Eq. 13 may be substituted into this factor to produce $$\sum_j f_j^{OBM} \ln(T_{2j}^{OBM,c}) - \sum_i f_i^V \ln(T_{2i}^{V,c}) = \quad (14)$$
$$\sum_j f_j^{OBM} \ln(B N_j^{-k} \overline{N}_{mix,c}^{-\gamma}) - \sum_i f_i^V \ln(B N_i^{-k} \overline{N}_{mix,c}^{-\gamma}).$$

Now, only the $\overline{N}_{mix,c}^{-\gamma}$ terms depend on the mixture. The $\overline{N}_{mix,c}^{-\gamma}$ terms may be canceled from each of the terms in Eq. 14, resulting in $$= \sum_j f_j^{OBM} \ln(B N_j^{-k}) - \sum_i f_i^V \ln(B N_i^{-k}). \quad (15)$$

None of the terms in Eq. 15 depends on properties of the mixture. Eq. 15 may be arranged into a form where Eq. 13 may be used to re-introduce $T_2$ terms of the OBMF and the virgin oil into the equation. First, mean chain length terms may be added and subtracted from Eq. 15 to produce $$= \sum_j f_j^{OBM} \ln(B N_j^{-k}) - \sum_i f_i^V \ln(B N_i^{-k}) + \quad (16)$$
$$\ln(\overline{N}_{OBM}^{-\gamma}) - \ln(\overline{N}_{OBM}^{-\gamma}) + \ln(\overline{N}_V^{-\gamma}) - \ln(\overline{N}_V^{-\gamma}),$$

which may be arranged into the form $$= \sum_j f_j^{OBM} \ln(B N_j^{-k} \overline{N}_{OBM}^{-\gamma}) - \sum_i f_i^V \ln(B N_i^{-k} \overline{N}_V^{-\gamma}) - \ln\left(\frac{\overline{N}_{OBM}}{\overline{N}_V}\right)^{-\gamma}. \quad (17)$$

Now, using the equations $$\sum_j f_j^{OBM} = \sum_i f_i^V = 1, \quad (18)$$

Eq. 17 may be arranged into the form $$= \ln(T_{2LM}^{OBM}) - \ln(T_{2LM}^V) + \gamma \ln\left(\frac{\overline{N}_{OBM}}{\overline{N}_V}\right) \quad (19)$$
$$= \ln\left(\frac{T_{2LM}^{OBM}}{T_{2LM}^V}\right) + \gamma \ln\left(\frac{\overline{N}_{OBM}}{\overline{N}_V}\right).$$

Now, the first term of Eq. 12 is considered. Eq. 13 may be substituted into the first term of Eq. 12, resulting in $$\sum_i f_i^V \ln(T_{2i}^{V,c}) = \quad (20)$$
$$\sum_i f_i^V \ln(B N_i^{-k} \overline{N}_{mix,c}^{-\gamma}) = \sum_i f_i^V \ln[B N_i^{-k} ((1-c)\overline{N}_V + c \overline{N}_{OBM})^{-\gamma}],$$

where the scaling law for alkanes has been used to replace the $\overline{N}_{mix,c}^{-\gamma}$ term. Dividing the second term of the logarithm by $\overline{N}_V$ results in $$= \sum_i f_i^V \ln(B N_i^{-k} \overline{N}_V^{-\gamma}) + \sum_i f_i^V \ln\left[\left(1 - c\left(\frac{\overline{N}_V - \overline{N}_{OBM}}{\overline{N}_V}\right)\right)^{-\gamma}\right]. \quad (21)$$

Eq. 13 and Eq. 18 can be used with Eq. 21 to produce $$= \ln(T_{2LM}^V) - \gamma \ln\left(1 - c\left(\frac{\overline{N}_V - \overline{N}_{OBM}}{\overline{N}_V}\right)\right). \quad (22)$$

Using a logarithmic Taylor series expansion, Eq. 22 becomes $$\sum_i f_i^V \ln(T_{2i}^{V,c}) \approx \ln(T_{2LM}^V) + \gamma c\left(\frac{\overline{N}_V - \overline{N}_{OBM}}{\overline{N}_V}\right) + \gamma \frac{c^2}{2}\left(\frac{\overline{N}_V - \overline{N}_{OBM}}{\overline{N}_V}\right)^2, \quad (23)$$

wherein the higher order (>2) terms are ignored as their values are very small.

Each of the terms in Eq. 12 have now been expressed independent of the mixture. Thus, Eq. 19 and Eq. 23 may be substituted into Eq. 12, resulting in $$\ln(T_{2LM}^{mix}) = \ln(T_{2LM}^V) + \quad (24)$$
$$c\left(\ln\frac{T_{2LM}^{OBM}}{T_{2LM}^V} + \gamma \ln\frac{\overline{N}_{OBM}}{\overline{N}_V} + \gamma\frac{\overline{N}_V - \overline{N}_{OBM}}{\overline{N}_V}\right) + c^2\frac{\gamma}{2}\left(\frac{\overline{N}_V - \overline{N}_{OBM}}{\overline{N}_V}\right)^2,$$

Generally, $$\left(\frac{\overline{N}_V - \overline{N}_{OBM}}{\overline{N}_V}\right)^2 < 1,$$

unless the virgin oil is gas or has mean chain length close to that of the OBMF. Therefore, the third term of equation 24 can be eliminated, resulting in $$\ln(T_{2LM}^{mix}) = \ln(T_{2LM}^V) + c\left(\ln\frac{T_{2LM}^{OBM}}{T_{2LM}^V} + \gamma \ln\frac{\overline{N}_{OBM}}{\overline{N}_V} + \gamma\frac{\overline{N}_V - \overline{N}_{OBM}}{\overline{N}_V}\right), \quad (25)$$

which is a linear equation in the general linear form of y=mx+b. The term in the parentheses is the slope of the linear equation, and thus Eq. 25 may be expressed as $$\ln(T_{2LM}^{mix}) = \ln(T_{2LM}^V) + cm, \quad (26)$$

which is the same equation as Eq. 4 previously disclosed.

Validation of Equation 25

The validity of Eq. 25 was tested with several dead oils and oil-base mud filtrates. Relaxation time measurements were performed in the laboratory using a 2-MHz Maran Big-2 NMR machine. The first data set consists of five mixtures of a dead crude oil having different concentrations of an ester-based OBMF. The physical properties of the mixtures are shown in Table 1.

TABLE 1

Physical Properties of a Crude Oil and its OBMF Mixtures

| Samples | | Viscosity (cp) at | |
|---|---|---|---|
| Oil (%) | OBMF (%) | 21.1° C. | $T_{1LM}$ (ms) |
| 0 | 100 | 7.59 | 317.5 |
| 100 | 0 | 338.40 | 12.1 |
| 90 | 10 | 153.50 | 15.9 |
| 75 | 25 | 69.02 | 30.8 |
| 60 | 40 | 37.22 | 63.9 |

Figure 7:
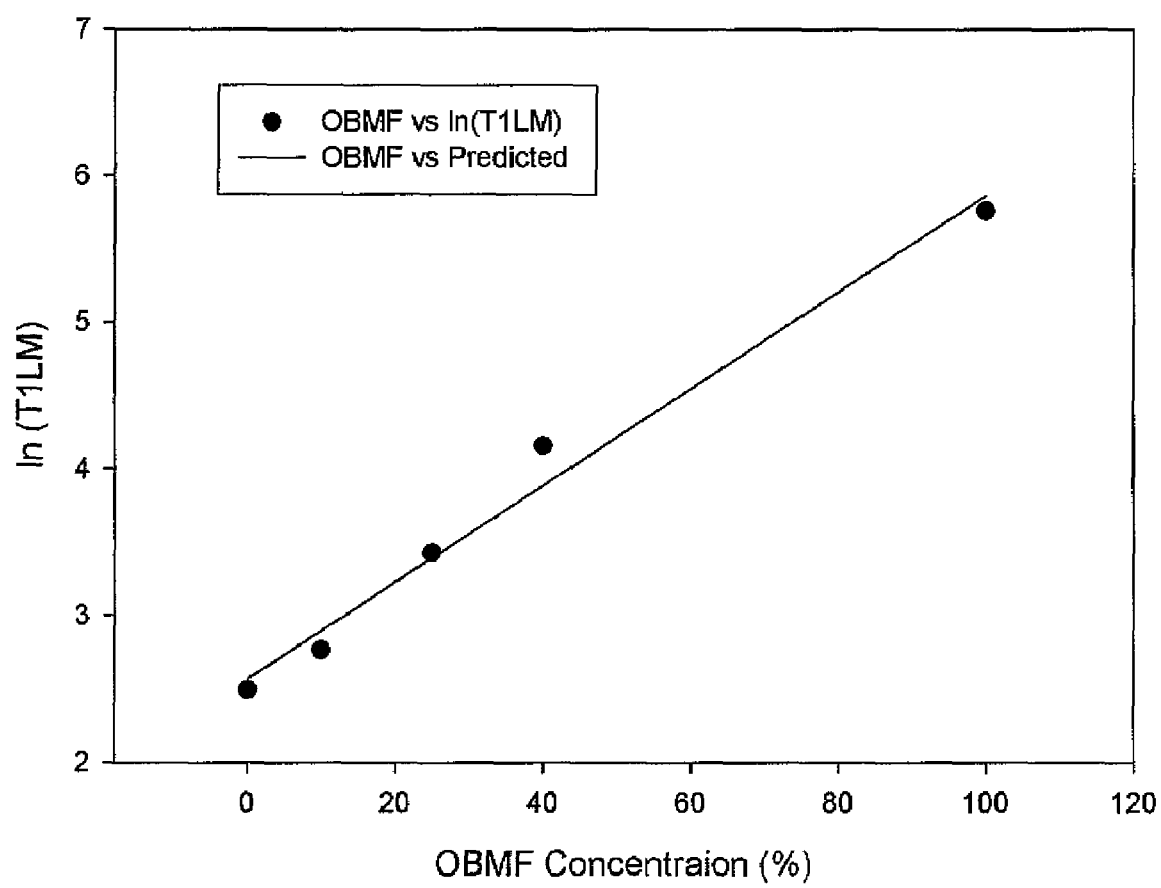
FIG. 7 shows the estimated relation derived for OBMF in heavy oil in accordance with the present invention.

FIG. 7 shows a plot of the $T_{1LM}$ measurements against the concentration of OBMF in the mixtures shown in Table 1. The data points corresponding to each of the five mixtures are plotted, and a least squares line has been fit to the data points to illustrate the linear relation.

The second data set consists of ten mixtures of a black oil mixed with one of three commercial OBM base oils A, B, and C, in different concentrations. This data set was taken from published literature (SPE Paper No. 71714), The physical properties of these mixtures are presented in Table 2.

TABLE 2

Physical Properties of a Black Oil and its Base Oil Mixtures

| Fluid | Base Oil | % Base Oil | Viscosity (cP)* | $T_{1LM}$ (ms) |
|---|---|---|---|---|
| | A | 100 | 3.55 | 726 |
| | B | 100 | 3.65 | 512 |
| | C | 100 | 1.61 | 776 |
| Black Oil | | 0 | 14.38 | 180 |
| Black Oil | A | 15 | 12.39 | 214 |
| Black Oil | A | 30 | 9.26 | 278 |
| Black Oil | B | 15 | 11.73 | 217 |
| Black Oil | B | 30 | 9.43 | 266 |
| Black Oil | C | 15 | 11.58 | 215 |
| Black Oil | C | 30 | 7.27 | 304 |

Figure 8:
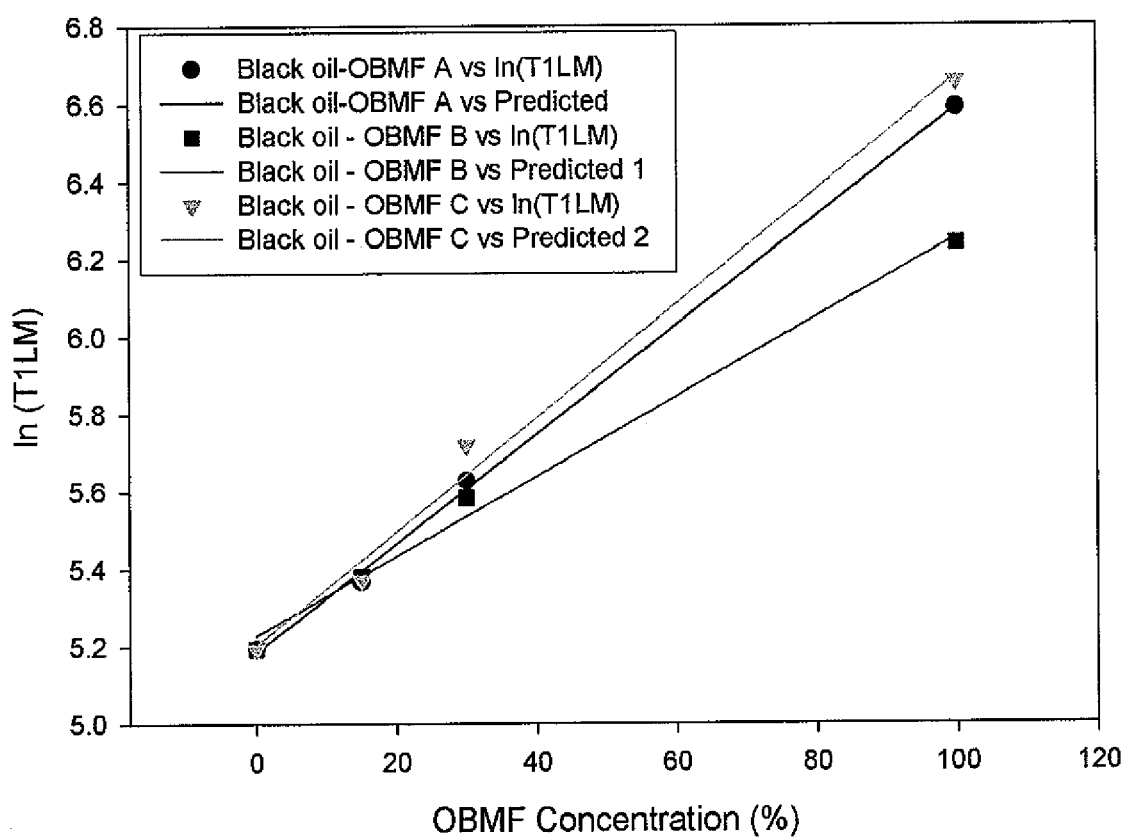
FIG. 8 shows the estimated relations derived for OBMF in black oils in accordance with the present invention.

FIG. 8 shows a plot of the $T_{1LM}$ measurements against the concentration of respective base oils in the mixtures shown in Table 2. The data points corresponding to each of the mixtures are plotted, and a least squares line has been fit to the set of data points corresponding to each base oil. Thus, the linear relation for each of the base oils is illustrated by one of three least squares lines.

The third data set consists of three different crude oils mixed with an olefin (D) as the OBMF contaminant. The mixtures for each of the crude oils have different concentrations of the OBMF contaminant. This data set was also taken from SPE Paper No. 71714. The physical properties of these mixtures are presented in Table 3,

TABLE 3

Physical Properties of 3 Crude Oils and their Base Oil Mixtures

| Fluid | Base Oil | % Base Oil | Viscosity (cP)* | $T_{1LM}$ (ms) |
|---|---|---|---|---|
| | D | 100 | 3.03 | 746 |
| Crude1 | | 0 | 3.03 | 662 |
| Crude1 | D | 5 | 2.21 | 630 |
| Crude1 | D | 20 | 2.09 | 642 |
| Crude1 | D | 40 | 2.31 | 634 |
| Crude1 | D | 75 | 2.69 | 621 |
| Crude2 | | 0 | 6.33 | 309 |
| Crude2 | D | 5 | 6.00 | 324 |
| Crude2 | D | 20 | 5.27 | 368 |

TABLE 3-continued

Physical Properties of 3 Crude Oils and their Base Oil Mixtures

| Fluid | Base Oil | % Base Oil | Viscosity (cP)* | $T_{1LM}$ (ms) |
|---|---|---|---|---|
| Crude2 | D | 40 | 4.24 | 425 |
| Crude2 | D | 75 | 3.21 | 548 |
| Crude3 |   | 0 | 171 | 23 |
| Crude3 | D | 5 | 121 | 30 |
| Crude3 | D | 20 | 50.1 | 62 |
| Crude3 | D | 40 | 18.1 | 137 |

Figure 9:
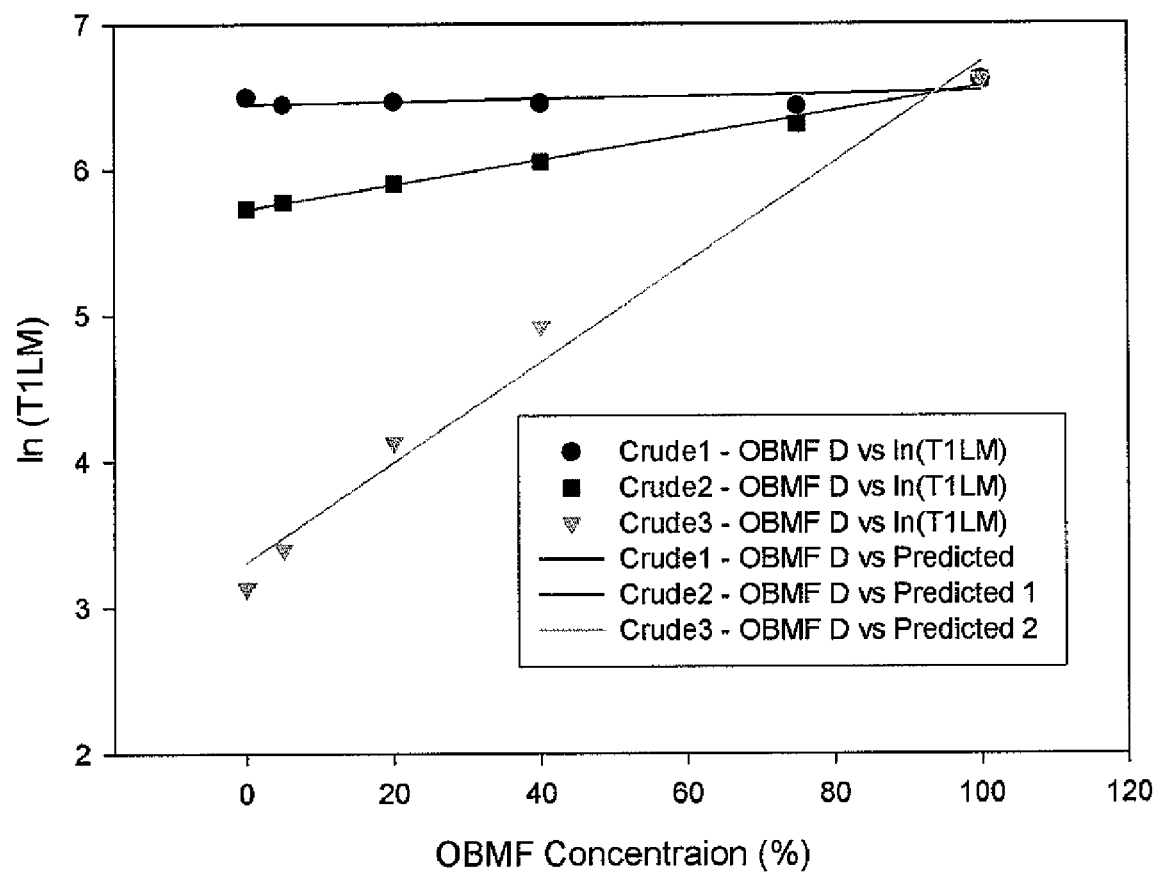
FIG. 9 shows the estimated relations derived for OBMF in crude oils in accordance with the present invention.

FIG. 9 shows a plot of the $T_{1LM}$ measurements against the concentration of respective base oils in the mixtures shown in Table 3. The data points corresponding to each of the mixtures are plotted, and a least squares line has been fit to the set of data points corresponding to each crude oil. Thus, the linear relation for each of the crude oils is illustrated by one of three least squares lines. Furthermore, it is important to note that olefins, such as the contaminant for the third data set, are unsaturated chemical compounds. In the previously disclosed derivation of the linear relation, some assumptions depended on the scaling law for alkanes. In contrast to olefins, alkanes are generally known to be saturated chemical compounds. Thus, the linear relation may also apply to non-alkane fluids, as illustrated in FIG. 9.

Embodiments of the present invention provide a method and apparatus to estimate the concentration of a known contaminant in a formation fluid using NMR measurements. Methods of the present invention may be practiced downhole or in a laboratory. Furthermore, in embodiments of the present invention, estimations of contamination are most accurate at low contamination levels (i.e., below 10%). Estimations of contamination levels below 10% are especially difficult for prior art methods. Also, methods of the present invention allow for the determination of both endpoints (i.e., 0% and 100% contamination) of a contaminant and hydrocarbon mixture.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for estimating a concentration of a substance in a test sample of formation fluid, comprising:
measuring an NMR parameter of a first sample of formation fluid to obtain a first measurement;
adding a known quantity of the substance to the first sample to produce a modified sample;
measuring the NMR parameter of the modified sample to obtain a second measurement; and
determining a relation between the concentration of the substance and a function of the NMR parameter using the first and second measurements and the NMR parameter of the substance.

2. The method of claim 1, wherein the first sample is the test sample, and the method further comprises using the determined relation to estimate the concentration of the substance in the test sample.

3. The method of claim 1, further comprising:
measuring the NMR parameter of a second sample to obtain a third measurement, wherein the second sample is the test sample; and
using the determined relation and the third measurement to estimate the concentration of the substance in the test sample.

4. The method of claim 1, further comprising measuring the NMR parameter of the substance.

5. The method of claim 1, wherein the method is performed in a wellbore.

6. The method of claim 5, wherein the first sample is the test sample, and the method further comprises using the determined relation to estimate the concentration of the substance in the test sample.

7. The method of claim 5, further comprising:
measuring the NMR parameter of a second sample to obtain a third measurement, wherein the second sample is the test sample; and
using the determined relation and the third measurement to estimate the concentration of the substance in the test sample.

8. The method of claim 1, wherein the relation is approximately linear.

9. The method of claim 1, wherein the determining a relation comprises computing the parameters of a line.

10. The method of claim 1, further comprising measuring the NMR parameter of additional modified samples to obtain additional measurements, and wherein the determining a relation comprises computing the parameters of the relation using the additional measurements.

11. The method of claim 1, wherein the NMR parameter is selected from the group consisting of $T_1$, $T_2$, diffusion constant, hydrogen index, and viscosity.

12. The method of claim 1, wherein the substance is an oil-base mud filtrate.

13. The method of claim 1, wherein the test sample comprises an oil-base mud filtrate and hydrocarbons.

14. A system for estimating a concentration of a substance in a test sample of formation fluid, comprising:
a mixer configured to add a known quantity of the substance to a first sample of formation fluid to produce a modified sample;
an NMR measurement device configured to measure an NMR parameter of the first sample and the modified sample to obtain a first measurement and a second measurement; and
a processor configured to determine a relation between the concentration of the substance and a function of the NMR parameter using the first and second measurements and the NMR parameter of the substance.

15. The system of claim 14, wherein the first sample is the test sample and the determined relation is used with the first measurement to estimate the concentration of the substance in the test sample.

16. The system of claim 14, wherein:
the NMR measurement device is further configured to measure the NMR parameter of a second sample of formation fluid to obtain a third measurement, wherein the second sample is the test sample; and
the determined relation is used with the third measurement to estimate the concentration of the substance in the test sample.

17. The system of claim 14, wherein the NMR measurement device is further configured to measure the NMR parameter of the substance.

18. The system of claim 14, further comprising a probe module disposed in a wellbore.

19. The system of claim 18, wherein the mixer is disposed in the wellbore.

20. The system of claim 19, wherein the NMR measurement device and the processor are disposed in the wellbore.

21. The system of claim 14, further comprising a downhole tool configured to extract samples of formation fluid.

22. A downhole tool for estimating a concentration of a substance in a test sample of formation fluid, comprising:
   a tool body adapted to be placed in a borehole;
   a mixing module disposed in the tool body and configured to add a known quantity of the substance to a first sample of formation fluid to produce a modified sample;
   an NMR module disposed in the tool body and configured to measure an NMR parameter of the first sample and the modified sample; and
   a processor disposed in the tool body and configured to determine a relation between the concentration of the substance and the NMR parameter.

23. The downhole tool of claim 22, wherein the first sample is the test sample and the determined relation is used to estimate the concentration of the substance in the test sample.

24. The downhole tool of claim 22, wherein:
   the NMR module is further configured to measure the NMR parameter of a second sample of formation fluid, wherein the second sample is the test sample; and
   the determined relation is used to estimate the concentration of the substance in the test sample.

25. The downhole tool of claim 22, further comprising a probe module disposed in the tool body and configured to extract samples of formation fluid.

* * * * *